(12) United States Patent
Tanaka et al.

(10) Patent No.: US 9,629,371 B2
(45) Date of Patent: Apr. 25, 2017

(54) METHOD FOR REDUCING DAMAGE BY HARMFUL ORGANISMS IN CORN CULTIVATION

(71) Applicant: SUMITOMO CHEMICAL COMPANY, LIMITED, Tokyo (JP)

(72) Inventors: Azusa Tanaka, Takarazuka (JP); Norihisa Sakamoto, Kasai (JP); Yasutaka Shimokawatoko, Takarazuka (JP)

(73) Assignee: SUMITOMO CHEMICAL COMPANY, LIMITED, Tokyo ( * ) Notice: Subject to any disclaimer, the term of this patent is extended or adjusted under 35 U.S.C. 154(b) by 0 days.

(21) Appl. No.: 14/109,295

(22) Filed: Dec. 17, 2013

(65) Prior Publication Data
US 2014/0187515 A1    Jul. 3, 2014

(30) Foreign Application Priority Data

Dec. 27, 2012  (JP) ................. 2012-284308

(51) Int. Cl.
| | | |
|---|---|---|
| A01N 57/00 | (2006.01) | |
| A01N 57/02 | (2006.01) | |
| A01N 57/10 | (2006.01) | |
| A01N 57/16 | (2006.01) | |
| A01N 43/78 | (2006.01) | |
| A01N 51/00 | (2006.01) | |

(52) U.S. Cl.
CPC ............. *A01N 57/16* (2013.01); *A01N 43/78* (2013.01); *A01N 51/00* (2013.01)

(58) Field of Classification Search
None
See application file for complete search history.

(56) References Cited

U.S. PATENT DOCUMENTS

| | | | |
|---|---|---|---|
| 4,198,782 A * | 4/1980 | Kydonieus et al. | ....... 47/58.1 R |
| 5,143,539 A * | 9/1992 | Lovell | ............ 504/103 |
| 2011/0110906 A1 | 5/2011 | Andersch et al. | |
| 2011/0174898 A1 | 7/2011 | Peyron | |
| 2014/0020610 A1* | 1/2014 | Sakamoto et al. | ............ 111/118 |
| 2014/0020611 A1 | 1/2014 | Sakamoto et al. | |

FOREIGN PATENT DOCUMENTS

| | | |
|---|---|---|
| CN | 1299596 A | 6/2001 |
| CN | 101697734 A | 4/2010 |
| CN | 102090416 A | 6/2011 |
| CN | 102630700 A | 8/2012 |
| JP | 4-112805 A | 4/1992 |
| JP | 2013-133308 A | 7/2013 |
| JP | 2013-133309 A | 7/2013 |
| JP | 2013133309 * | 7/2013 |
| WO | WO 2010/007239 A2 | 1/2010 |
| WO | WO 2010/022917 A2 | 3/2010 |
| WO | WO 2010/100638 A2 | 9/2010 |
| WO | WO-2010100638 * | 9/2010 |

OTHER PUBLICATIONS

Spanish Search Report dated Feb. 5, 2014 for Spanish Application No. 201331872 with English translation.
Wright et al., "Corn Insect Management," Entomological Society of America, 1999, pp. 10-21 and 44-119, ISBN: 0-938522-76-0.
Hungarian Search Report, issued Dec. 9, 2014, for Hungarian Application No. P1300742.
A machine translation of CN-101697734-A published on Apr. 28, 2010.
A Written Opinion (including an English translation) issued in the corresponding French Patent Application No. 1363536 on Aug. 27, 2015.
Office Action (including an English translation thereof) issued in the corresponding Hungarian Patent Application No. P1300742 on Jan. 25, 2016.
Office Action (including an English translation thereof) issued in the corresponding Hungarian Patent Application No. P1300742/19 on Jan. 4, 2017.

* cited by examiner

*Primary Examiner* — Alton Pryor
(74) *Attorney, Agent, or Firm* — Birch, Stewart, Kolasch & Birch, LLP

(57) ABSTRACT

Provided is a method for reducing damage by harmful organisms in corn cultivation. Damage by harmful organisms in corn cultivation can be reduced by carrying out the steps of: A) making a furrow in a cultivated land; B) seeding corn into the furrow formed in the foregoing step; C) applying to the furrow one or more selected from the below-mentioned compound group (I) and chlorpyrifos; and D) closing the furrow. compound group (I): group consisting of clothianidin, thiamethoxam, imidacloprid and thiacloprid.

20 Claims, No Drawings

METHOD FOR REDUCING DAMAGE BY HARMFUL ORGANISMS IN CORN CULTIVATION

BACKGROUND OF THE INVENTION

Field of the Invention

The present invention relates to a method for reducing damage by harmful organisms in corn cultivation.

Description of the Related Art

Previously, various methods have been known as a method for reducing damage by harmful organisms in corn cultivation.

PRIOR ART LITERATURE

Non-Patent Literature

Non-Patent Literature 1: Handbook of Corn Insects. ISBN: 0-938522-76-0., 1999. Entomological Society of America

SUMMARY OF THE INVENTION

In corn cultivation, with worldwide cereal demand expansion, various efforts have been made in order to increase a yield, but since a reduction in yield due to harmful organisms such as pests and weeds has been significant, development of a method for reducing damage by harmful organisms in corn cultivation has been desired.

The present inventors have conducted studies for finding out a method for reducing damage by harmful organisms in corn cultivation, and resultantly found out that damage by harmful organisms in corn cultivation can be reduced by carrying out the steps of: A) making a furrow in a cultivated land (hereinafter, referred to as step A in some cases); B) seeding corn into the furrow formed in the foregoing step (hereinafter, referred to as step B in some cases); C) applying to the furrow one or more selected from the below-mentioned compound group (I) (hereinafter, referred to as the present compound (I) in some cases) and chlorpyrifos (hereinafter, referred to as step C in some cases); and D) closing the furrow (hereinafter, referred to as step D in some cases).

That is, the present invention is as follows:

[1] A method for reducing damage by harmful organisms in corn cultivation, the method including the steps of: A) making a furrow in a cultivated land; B) seeding corn into the furrow formed in the foregoing step; C) applying to the furrow one or more selected from the below-mentioned compound group (I) and chlorpyrifos; and D) closing the furrow. compound group (I): group consisting of clothianidin, thiamethoxam, imidacloprid and thiacloprid.

[2] The method according to [1], wherein the step of applying one or more selected from the compound group (I) and chlorpyrifos is a step of applying a composition containing one or more selected from the compound group (I) and a composition containing chlorpyrifos.

[3] The method according to [2], wherein the composition containing one or more selected from the compound group (I) is a granule or micro-granule containing one or more selected from the compound group (I).

[4] The method according to [2], wherein the composition containing one or more selected from the compound group (I) is an aqueous dispersion or aqueous solution containing one or more selected from the compound group (I).

[5] The method according to any one of [2] to [4], wherein the composition containing chlorpyrifos is a granule or micro-granule containing chlorpyrifos.

[6] The method according to any one of [2] to [4], wherein the composition containing chlorpyrifos is an aqueous dispersion or aqueous solution of chlorpyrifos.

[7] The method according to [4], wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (I).

[8] The method according to [6], wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains chlorpyrifos.

[9] The method according to [1], wherein the step of applying one or more selected from the compound group (I) and chlorpyrifos is a step of applying a composition containing one or more selected from the compound group (I) and chlorpyrifos.

[10] The method according to [9], wherein the composition containing one or more selected from the compound group (I) and chlorpyrifos is a granule or micro-granule containing one or more selected from the compound group (I) and chlorpyrifos.

[11] The method according to [9], wherein the composition containing one or more selected from the compound group (I) and chlorpyrifos is an aqueous dispersion or aqueous solution containing one or more selected from the compound group (I) and chlorpyrifos.

[12] The method according to [11], wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains one or more selected from the compound group (I) and chlorpyrifos.

[13] The method according to any one of [1] to [12], wherein the land is ditched to a depth of 1 to 10 cm.

[14] The method according to any one of [1] to [13], wherein ditching is performed using a disk furrow opener.

[15] The method according to any one of [1] to [14], wherein seeding is performed using a pneumatic seeder.

According to the present invention, harmful organisms in corn cultivation can be prevented; therefore, damage by the harmful organisms in corn cultivation can be reduced.

DETAILED DESCRIPTION OF THE PREFERRED EMBODIMENTS

For the order of carrying out steps, usually, a step A, and then steps B and C are carried out. In the step A, usually, a furrow having a V-shaped cross section is formed in a linear shape on a cultivated land. The step A may be carried out, followed by carrying out the step B, and then the step C, or the order may be reversed. The steps B and C may be carried out in parallel. Usually, a step D is carried out after the steps B and C.

In the present invention, usually, a seeder which is pulled with a tractor is used. Examples of the seeder include a composite-type seeder including a ditching part for forming a furrow, a seeding part for seeding a furrow in a speed linkage manner through piping from a hopper box filled with a seed, agricultural chemical application part for applying the present compound (I) and chlorpyrifos in a speed linkage manner through piping from one or more reservoirs filled with the present compound (I) and chlorpyrifos collectively or separately, a furrow closing part for closing the furrow by gathering together a soil on the side of the formed furrow, and so on.

The ditching part of a seeder is usually attached to a front part of the seeder, and a furrow is formed on a cultivated land with movement of a tractor. Examples of the ditching part include a ploughshare furrow opener and a disk furrow opener, and a ditching system using a disk furrow opener which has a strong force of cutting a crop residue, has a small reduction in a cutting force due to adhesion of a soil, and can stabilize the depth of a furrow is preferable in that a furrow can be seeded and a chemical can be applied to the furrow uniformly due to stabilization of a depth of a furrow, so that the effect of the chemical is stabilized.

The depth of the furrow formed on a cultivated land can be appropriately changed depending on the soil condition of a place of corn cultivation, the condition of cultivating corn thereafter, and the weather condition, and is usually 1 to 10 cm, preferably 2 to 8 cm, further preferably 2 to 6 cm.

The seeding part of the seeder is usually attached to a rear of the ditching part, and the furrow is seeded with movement of a tractor. Examples of the seeding part include a mechanical seeder and a pneumatic seeder, and the pneumatic seeder using air pressure is preferable in that seed clogging or seeding leakage is small, so that seeding is stably performed, and seeds can be planted in a furrow in order. Examples of the pneumatic seeder include a vacuum suction type seeder and a blowing type seeder, and based on the reason of imparting little damage to a seed, a vacuum suction type seeder is preferable.

Clothianidin is a known compound, and is described in, for example, "The Pesticide Manual-15$^{th}$ edition (published by BCPC); ISBN 978-1-901396-18-8", page 229. This compound is obtained from a commercially available preparation, or is obtained by production through a known method.

Thiamethoxam is a known compound, and is described in, for example, "The Pesticide Manual-15$^{th}$ edition (published by BCPC); ISBN 978-1-901396-18-8", page 1112. This compound is obtained from a commercially available preparation, or is obtained by production through a known method.

Imidacloprid is a known compound, and is described in, for example, "The Pesticide Manual-15$^{th}$ edition (published by BCPC); ISBN 978-1-901396-18-8", page 645. This compound is obtained from a commercially available preparation, or is obtained by production through a known method.

Thiacloprid is a known compound, and is described in, for example, "The Pesticide Manual-15$^{th}$ edition (published by BCPC); ISBN 978-1-901396-18-8", page 1111. This compound is obtained from a commercially available preparation, or is obtained by production through a known method.

Chlorpyrifos is a known compound, and is described in, for example, "The Pesticide Manual-15$^{th}$ edition (published by BCPC); ISBN 978-1-901396-18-8", page 203. This compound is obtained from a commercially available preparation, or is obtained by production through a known method.

In the present invention, the present compound (I) may be used as such, but is usually formulated into an arbitrary dosage form such as a granule, a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable by mixing the present compound (I) with an appropriate solid carrier or liquid carrier, and adding a surfactant and other formulation additives for a preparation as necessary.

Like the present compound (I), chlorpyrifos may be used as such, but is usually formulated and used.

In the present invention, a preparation containing the present compound (I) and chlorpyrifos (hereinafter, referred to as the present preparation in some cases) may be used, or a preparation containing the present compound (I) (hereinafter, referred to as the present preparation (I) in some cases) and a preparation containing chlorpyrifos (hereinafter, referred to as the present preparation (II) in some cases) may be used in combination.

In the present invention, when the present preparation (I) and the present preparation (II) are used in combination, the present preparation (I) and the present preparation (II) may be used individually, or may be mixed and used. The dosage forms of the present preparation (I) and the present preparation (II) may be the same, or may be different.

Examples of the solid carrier used upon formulation into a preparation include natural or synthetic minerals such as clay, kaolin, talc, bentonite, sericite, sulfur, active carbon, calcium carbonate, diatomaceous earth, quartz, pumice stone, calcite, meerschaum, dolomite, olivine, pyroxene, amphibole, feldspar, silica, alumina, vermiculite, and perlite; and fine grains of an elastomer, a plastic, a ceramic, a metal, sawdust, corncob, a kernel shell of coconut, a stem of tobacco and the like.

Examples of the liquid carrier include water, xylene, methanol, butanol, pentanol, benzyl alcohol, cyclohexanone, gamma-butyrolactone, N-methyl-pyrrolidone, N-octyl-pyrrolidone, glycol diacetate, glycols, fatty acid dimethylamides, fatty acids and fatty acid esters. They may be mixed and used.

Examples of the surfactant include common nonionic surfactants, cationic surfactants, anionic surfactants and amphoteric surfactants, and one kind or two or more kinds thereof are used.

Examples of the surfactant include an alkylsulfuric acid salt, an alkylsulfuric acid ester salt, an alkylsulfonic acid salt, an alkylarylsulfonic acid salt, a lignosulfonic acid ester, a naphthalenesulfonic acid salt, a phenolsulfonic acid salt, a dibutylnaphthalenesulfonic acid salt, a fatty alcohol sulfuric acid salt, fatty acid alkyl aryl ethers and polyoxyethylene compounds thereof, polyethylene glycol ethers, polyethylene glycol fatty acid esters, polyhydric alcohol esters, a sugar alcohol derivative and a silicone-based surfactant.

Examples of the other auxiliary agents for a preparation include an emulsifier, a dispersant, an antifoamer, a stabilizer, an antiseptic and a colorant.

Examples of the preferred emulsifier include a nonionic emulsifier and an anionic emulsifier (e.g., a polyoxyethylene fatty alcohol ether, an alkyl sulfonate and an aryl sulfonate). Examples of the dispersant include a lignin sulfurous acid waste liquid and methyl cellulose.

Examples of the preferred antifoamer include silicone or magnesium stearate-based antifoamers.

Examples of the colorant include red dyes, blue dyes, green dyes and yellow dyes. Specific examples include Monazole Red, Cyanine Green, Prussian Blue and Brilliant Blue. Particularly, in the case of a granule, it is preferable to add a colorant because the granule is easily identified at the time of application or after application.

Further, for example, glycerin, ethylene glycol and propylene glycol may be added as an antifreezing agent.

When a granule is used in the step C of the present invention, it is applied as such without being diluted.

The granule can be a form such as a fine granule, a macro granule, or a micro-granule, by changing the particle size thereof.

The content of the present compound (I) in the granule is usually 0.01 to 20% by weight, preferably 0.05 to 10% by weight, further preferably 0.1 to 5% by weight.

The content of chlorpyrifos in the granule is usually 0.1 to 30% by weight, preferably 0.5 to 20% by weight, further preferably 1 to 10% by weight.

When a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable is used in the step C of the present invention, an aqueous dispersion or aqueous solution obtained by dispersing or dissolving any of the aforementioned preparations in water is usually applied. The aqueous dispersion or aqueous solution may contain herbicide, a safener and the like.

The aqueous dispersion of the present compound (I) in the present invention includes a liquid formed by suspending the present compound (I) in water in a solid state, and a liquid formed by emulsifying the present compound (I) in water in a liquid state. The same holds true for the aqueous dispersion of chlorpyrifos.

The application amount of the present compound (I) in the present invention can be appropriately changed depending on the condition of cultivating corn thereafter and the weather condition, and is usually 5 to 500 g, preferably 10 to 400 g, further preferably 10 to 200 g per hectare of a cultivated land which is seeded with corn.

The application amount of chlorpyrifos in the present invention can be appropriately changed depending on the condition of cultivating corn thereafter and the weather condition, and is usually 10 to 3000 g, preferably 40 to 1500 g, further preferably 50 to 1200 g per hectare of a cultivated land which is seeded with corn.

The ratio of the application amounts of the present compound (I) and chlorpyrifos in the present invention is usually 50:1 to 1:600, preferably 10:1 to 1:150, further preferably 4:1 to 1:50 in terms of a weight ratio.

Usually, the present compound (I) and chlorpyrifos are stored in a tank attached to a tractor body or a seeder pulled with a tractor, and is applied, in linkage with or independently of a vehicle speed, through piping from the tank with movement of the tractor.

When a granule or micro-granule containing the present compound (I) or an aqueous dispersion or aqueous solution of chlorpyrifos is used in the step C, the present compound (I) and chlorpyrifos are both applied into the furrow, but usually the present compound (I) and chlorpyrifos are stored separately in two reservoir, and each applied into the furrow. The granule or micro-granule containing the present compound (I) may be applied before or after seeding, but is preferably applied before seeding. The aqueous dispersion or aqueous solution of chlorpyrifos may be applied before or after seeding, but is preferably applied in parallel with seeding or after seeding, so that the aqueous dispersion or aqueous solution of chlorpyrifos is in direct contact with the seed. When the present compound (I) and chlorpyrifos are stored separately in two chemical tanks, positions of chemical nozzles are adjusted to perform application orderly so that the compounds do not interfere with each other during application.

Application is performed by a similar operation when the aqueous dispersion or aqueous solution of the present compound (I) and the granule or micro-granule containing chlorpyrifos are applied.

When the aqueous dispersion or aqueous solution of the present compound (I) and chlorpyrifos is applied, the type of application is not particularly limited as long as it is capable of application into a furrow, but particularly spraying, dripping or drenching is preferable.

When the type of application is spraying, dripping or drenching, by applying pressure with a pump or adjusting the opening of a valve of a tank or a hose, the application amount can be adjusted to perform uniform application to a furrow.

The furrow closing part is usually made of rubber or made of cast iron, has a wheel shape, and closes a furrow by gathering together on the side of the furrow with movement of a tractor.

The present invention can reduce damage by harmful organisms in corn cultivation.

In the present invention, the harmful organism refers to pests, weeds and the like.

Specific examples of vermin which can be controlled by the present invention include vermin belonging to *Agriotes* spp., *Diabrotica* spp., *Agrotis* spp., *Myzus* spp., *Aphis* spp., *Ostrinia* spp., *Zyginidia* spp., *Sesamia* spp., *Oscinella* spp., *Sitobion* spp., *Scutigerella* spp., *Astylus* spp., *Rhopalosiphum* spp., *Metopolophium* spp., *Melanotus* spp. and *Melolontha* spp., and the present invention is preferably applied as a method for reducing damage by particularly *Agriotes* spp., *Diabrotica* spp., *Agrotis* spp. and *Rhopalosiphum* spp.

The variety of corn, to which the present invention can be applied, is not particularly limited, but application of corn to a hybrid variety is preferable. The hybrid variety is first cross obtained by mating two different type of varieties, and generally has more excellent characteristics than those of both parents.

Corn may be corn to which resistance has been imparted by a genetic engineering technique or a breeding method by mating.

The corn seed used in the present invention is preferably treated with a fungicide, and examples of the fungicide include fludioxonil, metalaxyl, metalaxyl-M, thiuram, triticonazole, carboxin, prochloraz, prothioconazole, sedaxane, penflufen, fluxapyroxad, trifloxystrobin, pyraclostrobin and difenoconazole, and fludioxonil, metalaxyl-M, thiuram, triticonazole, sedaxane, penflufen, and fluxapyroxad are preferable, and fludioxonil, metalaxyl-M and thiuram are more preferable. The corn seed is used after treated with one or more kinds of these fungicides. Alternatively, a commercially available treated seed may be purchased and used.

The corn seed used in the present invention may be treated with a safener. Examples of the safener include isoxadifen-ethyl, furilazole, dichlormid, benoxacor and cyprosulfamide. The corn seed is used after treated with one or more kinds of these safeners.

The corn seed used may be treated with a safener and the aforementioned fungicide.

In the present invention, instead of using a corn seed treated with the safener, the safener may be applied to the furrow formed in the step A before or after or in parallel with the step B, or the safener may be applied to the cultivated land before the step A or after the step D.

In the present invention, it is preferable to apply a herbicide to a cultivated land before the step A or after the step D in order to suppress generation of weeds during a cultivation term of corn, and examples of the herbicide include mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluoroxypyr, pethoxamid, flumioxazin, thiencarbazone-methyl, iodosulfuron-methyl-sodium salt, prosulfuron, topramezone, metosulam, cycloxydim, aclonifen, dimethenamid, florasulam, clopyralid, flazasulfuron, imazamox, MCPA, 2.4-D, linuron, propisochlor, thifensulfuron methyl and tritosulfuron; preferably mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluoroxypyr, pethoxamid, flumioxazin, thiencarbazone-methyl, iodosulfuron-methyl-sodium salt, prosulfuron, topramezone, metosulam, cycloxydim and aclonifen; more preferably mesotrione, nicosulfuron, S-metolachlor, acetochlor, terbuthylazine, sulcotrione, isoxaflutole, bromoxynil, dicamba, foramsulfuron, dimethenamid-P, rimsulfuron, bentazon, glyphosate, tembotrione, pendimethalin, flufenacet, fluoroxypyr, pethoxamid, flumioxazin, thiencarbazone-methyl and iodosulfuron-methyl-sodium salt. Usually, one or more of these herbicides are applied. When two or more thereof are applied, they may be applied simultaneously, or they may be applied separately. When they are applied separately, they may be applied on the same day, or on another day.

These herbicides may be applied by, if necessary, mixing with a safener. As such safeners, the aforementioned safeners can be used.

EXAMPLES

Next the present invention will be further described by way of the following examples, but the present invention is not limited to these examples.

Example 1

A clothianidin granule (using a 0.7% granule, manufactured by Sumitomo Chemical Company, Limited), a thiamethoxam granule (using a 0.5% granule, trade name: Actara Granule 5, manufactured by Syngenta Japan K.K.), an imidacloprid granule (using a 1.0% granule, trade name: Admirer 1 Granule, manufactured by Bayer CropScience K.K.) or a thiacloprid granule (using a 1.0% granule, trade name: BARIARD Box Granule, manufactured by Nihon Nohyaku Co., Ltd.) and a chlorpyrifos granule (using a 3.0% granule, trade name: Dursban Granule, manufactured by Nissan Chemical Industries, Ltd.) were mixed in the combination described in Tables 1 and 2.

A container was filled with a soil, a furrow was formed to a depth of 3 cm from the soil surface, the prepared mixed granule was, respectively, applied in the chemical amount described in columns 1 to 27 of Tables 1 and 2, corn (variety name: Pioneer 31P41, hybrid variety; seeds treated with metalaxyl and fludioxonil were used) were seeded in the furrow in an amount of one seed per container for each of the combinations described in columns 1 to 27 of Table 1 and 2, and a soil on the side of the furrow was gathered together to close the furrow. Corn was grown in a green house.

8 days after seeding of corn, 20 bird-cherry oat aphids (*Rhopalosiphum padi*) were released in each container. This is called a treatment section.

On the other hand, except that a mixed granule was not applied, corn was grown in a green house in the same manner as in the treatment section, and 20 bird-cherry oat aphids (*Rhopalosiphum padi*) were released. This is called a non-chemical-treatment section.

3 days after insect release, the number of aphids was investigated, and a preventive value was calculated using the following equation. The results are shown in Tables 1 and 2.

preventive value=$100 \times (A-B)/A$

A: number of insects during investigation of non-chemical-treatment section

B: number of insects during investigation of treatment section

TABLE 1

|   | The present compound (I) | Chlorpyrifos | Preventive value |
|---|---|---|---|
| 1 | Clothianidin 12.5 ga.i./ha | 125 ga.i./ha | 100 |
| 2 | Clothianidin 12.5 ga.i./ha | 250 ga.i./ha | 100 |
| 3 | Clothianidin 12.5 ga.i./ha | 500 ga.i./ha | 100 |
| 4 | Clothianidin 25 g a.i./ha | 125 ga.i./ha | 100 |
| 5 | Clothianidin 25 g a.i./ha | 250 ga.i./ha | 100 |
| 6 | Clothianidin 25 g a.i./ha | 500 ga.i./ha | 100 |
| 7 | Clothianidin 50 g a.i./ha | 125 ga.i./ha | 100 |
| 8 | Clothianidin 50 g a.i./ha | 250 ga.i./ha | 100 |
| 9 | Clothianidin 50 g a.i./ha | 500 ga.i./ha | 100 |
| 10 | Imidacloprid 50 g a.i./ha | 125 ga.i./ha | 100 |
| 11 | Imidacloprid 50 g a.i./ha | 250 ga.i./ha | 100 |
| 12 | Imidacloprid 50 g a.i./ha | 500 ga.i./ha | 100 |
| 13 | Imidacloprid 250 g a.i./ha | 125 ga.i./ha | 100 |
| 14 | Imidacloprid 250 g a.i./ha | 250 ga.i./ha | 100 |

TABLE 2

|   | The present compound (I) | Chlorpyrifos | Preventive value |
|---|---|---|---|
| 15 | Imidacloprid 250 g a.i./ha | 500 ga.i./ha | 100 |
| 16 | Thiamethoxam 25 g a.i./ha | 125 ga.i./ha | 100 |
| 17 | Thiamethoxam 25 g a.i./ha | 250 ga.i./ha | 100 |
| 18 | Thiamethoxam 25 g a.i./ha | 500 ga.i./ha | 100 |
| 19 | Thiamethoxam 125 g a.i./ha | 125 ga.i./ha | 100 |
| 20 | Thiamethoxam 125 g a.i./ha | 250 ga.i./ha | 100 |
| 21 | Thiamethoxam 125 g a.i./ha | 500 ga.i./ha | 100 |
| 22 | Thiacloprid 50 g a.i./ha | 125 ga.i./ha | 100 |
| 23 | Thiacloprid 50 g a.i./ha | 250 ga.i./ha | 100 |
| 24 | Thiacloprid 50 g a.i./ha | 500 ga.i./ha | 100 |

TABLE 2-continued

| | The present compound (I) | Chlorpyrifos | Preventive value |
|---|---|---|---|
| 25 | Thiacloprid 500 g a.i./ha | 125 ga.i./ha | 100 |
| 26 | Thiacloprid 500 g a.i./ha | 250 ga.i./ha | 100 |
| 27 | Thiacloprid 500 g a.i./ha | 500 ga.i./ha | 100 |

Example 2

An aqueous solution or aqueous dispersion of a clothianidin water dispersible granule (using a 50% water dispersible granule, trade name: DANTOP, manufactured by PhilagroFrance S.A.S.), a thiamethoxam water dispersible granule (using a 10.0% preparation, trade name: Actara Water Dispersible Granule, manufactured by Syngenta Japan K.K.), an imidacloprid water dispersible granule (using a 50.0% preparation, trade name: Admirer Water Dispersible Granule, manufactured by Bayer CropScience K.K.) or a thiacloprid water dispersible granule (using a 30.0% preparation, BARIARD Water Dispersible Granule, manufactured by Bayer CropScience K.K.) is mixed with an aqueous dispersion of a chlorpyrifos wettable powder (using a 25.0% preparation, trade name: Dursban Wettable Powder 25 manufactured by The Dow Chemical Company) in combinations described in Tables 3 and 4.

A container is filled with a soil, a furrow is formed to a depth of 3 cm from the soil surface, the prepared liquid chemical is applied in an application amount of 100 L/ha, the furrow is then seeded with corn (variety name: Pioneer, hybrid variety), and a soil on the side of the furrow is gathered together to close the furrow. Corn is grown in a green house.

10 days after seeding of corn, 10 bird-cherry oat aphids (*Rhopalosiphum padi*) were released. This is called a treatment section.

On the other hand, except that a liquid chemical is not applied, corn is grown in a green house in the same manner as in the treatment section, and 10 bird-cherry oat aphids (*Rhopalosiphum padi*) were released. This is called a non-chemical-treatment section.

3 days after insect release, the number of aphids is investigated, and a preventive value is calculated using the following equation.

preventive value=100×(A−B)/A

A: number of insects during investigation of non-chemical-treatment section
B: number of insects during investigation of treatment section As a result, the treatment section shows a high preventive value as compared to the non-treatment section, and is found to have reduced damage by harmful organisms in corn cultivation.

TABLE 3

| The present compound (I) | Chlorpyrifos |
|---|---|
| Clothianidin 12.5 ga.i./ha | 125 ga.i./ha |
| Clothianidin 12.5 ga.i./ha | 250 ga.i./ha |
| Clothianidin 12.5 ga.i./ha | 500 ga.i./ha |
| Clothianidin 25 g a.i./ha | 125 ga.i./ha |
| Clothianidin 25 g a.i./ha | 250 ga.i./ha |
| Clothianidin 25 g a.i./ha | 500 ga.i./ha |
| Clothianidin 50 g a.i./ha | 125 ga.i./ha |
| Clothianidin 50 g a.i./ha | 250 ga.i./ha |
| Clothianidin 50 g a.i./ha | 500 ga.i./ha |
| Imidacloprid 50 g a.i./ha | 125 ga.i./ha |
| Imidacloprid 50 g a.i./ha | 250 ga.i./ha |
| Imidacloprid 50 g a.i./ha | 500 ga.i./ha |
| Imidacloprid 250 g a.i./ha | 125 ga.i./ha |
| Imidacloprid 250 g a.i./ha | 250 ga.i./ha |

TABLE 4

| The present compound (I) | Chlorpyrifos |
|---|---|
| Imidacloprid 250 g a.i./ha | 500 ga.i./ha |
| Thiamethoxam 25 g a.i./ha | 125 ga.i./ha |
| Thiamethoxam 25 g a.i./ha | 250 ga.i./ha |
| Thiamethoxam 25 g a.i./ha | 500 ga.i./ha |
| Thiamethoxam 125 g a.i./ha | 125 ga.i./ha |
| Thiamethoxam 125 g a.i./ha | 250 ga.i./ha |
| Thiamethoxam 125 g a.i./ha | 500 ga.i./ha |
| Thiacloprid 50 g a.i./ha | 125 ga.i./ha |
| Thiacloprid 50 g a.i./ha | 250 ga.i./ha |
| Thiacloprid 50 g a.i./ha | 500 ga.i./ha |
| Thiacloprid 500 g a.i./ha | 125 ga.i./ha |
| Thiacloprid 500 g a.i./ha | 250 ga.i./ha |
| Thiacloprid 500 g a.i./ha | 500 ga.i./ha |

Example 3

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid chemical of thiencarbazone-methyl and isoxaflutole, each of which being a herbicide, at 150 L/ha so that the application amounts of thiencarbazone-methyl and isoxaflutole are 9.2 g/ha and 23 g/ha, respectively.

21 days after fertilization, using a pneumatic seeder (disk furrow opener), a cultivated land is ditched at intervals of 75 cm to a depth of 5 cm from the soil surface, and a mixed granule of clothianidin and chlorpyrifos is applied to the furrow so as to achieve an application amount of 30 g/ha for clothianidin and 250 g/ha for chlorpyrifos. After application, corns are seeded in the furrow (*Zea Mays*: hybrid variety). The furrow is seeded at intervals of 20 cm using, as a seed of corn, one treated with thiuram and cyprosulfamide which is a safener. A seeding density of corn is 70000 seeds/ha. After the furrow is seeded with corn, a soil on the side of the furrow is gathered together to close the furrow. This is called a treatment section.

For comparison, the furrow is seeded with corn by the operation same as that in the treatment section except that clothianidin and chlorpyrifos are not applied. This is called a non-treatment section.

In any section, four places are arranged by a randomized block method, with one place having an area of 45 m² (15 m×3 m).

17 days after application of clothianidin and chlorpyrifos, the number of corn plants germinated is investigated, with central two rows of four rows of seeded furrows as an investigation section, for the treatment section and the non-treatment section. 165 days after application of clothianidin and chlorpyrifos, the number of corn plants lodged due to damage by *Diabrotica virgifera* virgifera and *Agriotes lineatus* in the rows of the treatment section and the non-treatment section where the number of corn plants germinated is investigated, a lodge rate is calculated in accordance with the following equation, and then an average lodge rate for the four investigation sections is determined.

Lodge rate(%)=[(number of corn plants lodged)/ (number of corn plants germinated)]×100

As a result, the treatment section shows a low lodge rate as compared to the non-treatment section, and is found to have reduced damage by harmful organisms in corn cultivation.

Example 4

A chemical fertilizer (N:P:K=15:15:15) is applied to the soil surface of a cultivated land at 300 kg/ha, and the cultivated land is then plowed.

21 days after fertilization, using a pneumatic seeder (disk furrow opener) equipped with a power sprayer, a cultivated land is ditched at intervals of 75 cm to a depth of 3 cm from the soil surface, and a chlorpyrifos granule is applied to the furrow such that the application amount of chlorpyrifos is 500 g/ha. After application, corns (*Zea Mays*: hybrid variety) with which treated with thiuram, are seeded in the furrow 20 cm apart in rows. A seeding density of corn is 70000 seeds/ha. In parallel with seeding of corn, the furrow is spray-treated with an aqueous dispersion of thiacloprid at 150 L/ha so that the application amount of thiacloprid is 100 g/ha, with the liquid chemical being in direct contact with the seed, and a soil on the side of the furrow is then gathered together to close the furrow. After the furrow is closed, the soil surface of the whole cultivated land before germination of corn is spray-treated with a mixed liquid chemical of thiencarbazone-methyl and isoxaflutole, each of which being a herbicide, and cyprosulfamide which is a safener at 150 L/ha so that the application amounts of thiencarbazone-methyl, isoxaflutole and cyprosulfamide are 9.2 g/ha, 23 g/ha and 15 g/ha, respectively, for suppressing generation of weeds. This is called a treatment section.

For comparison, corns are seeded by the operation same as that in the treatment section except that chlorpyrifos and thiacloprid are not applied. This is called a non-treatment section.

In any section, four places are arranged by a randomized block method, with one place having an area of 45 m² (15 m×3 m).

17 days after application of chlorpyrifos and thiacloprid, the number of corn plants germinated is investigated, with central two rows of four rows of seeded furrows as an investigation section, for the treatment section and the non-treatment section. 165 days after application of chlorpyrifos and thiacloprid, the number of corn plants lodged due to damage by *Diabrotica virgifera* virgifera and *Agriotes lineatus* in the rows of the treatment section and the non-treatment section where the number of corn plants germinated is investigated, a lodge rate is calculated in accordance with the following equation, and then an average lodge rate for the four investigation sections is determined.

Lodge rate(%)=[(number of corn plants lodged)/ number of corn plants germinated)]×100

As a result, the treatment section shows a low lodge rate as compared to the non-treatment section, and is found to have reduced damage by harmful organisms in corn cultivation.

Example 5

Ammonium phosphate (N:P:K=12:52:0) and urea (N:P:K=46:0:0), each of which being a fertilizer, are applied to the soil surface of a cultivated land at 100 kg/ha and 260 kg/ha, respectively, and the cultivated land is then plowed.

In order to prevent generation of weeds, 28 days after fertilization, the whole cultivated land is spray-treated with a mixed agent (using 610 g/kg water dispersible granule, trade name: MaisTer, manufactured by Bayer CropScience K.K.) of foramsulfuron and an iodosulfuron-methyl-sodium salt, each of which being a herbicide, and a safener, isoxadifen-ethyl, at 0.15 L/ha in terms of an application amount of the preparation.

3 days after application of the preparation, using a pneumatic seeder (disk furrow opener) equipped with a power sprayer, a cultivated land is ditched at intervals of 75 cm to a depth of 4 cm from the soil surface, and the furrow is seeded with corn (*Zea Mays*; hybrid variety). The cultivated land is seeded at intervals of 20 cm using, as a corn seed, one treated with a mixed agent of metalaxyl-M and fludioxonil (trade name: Maxim XL, manufactured by Syngenta Japan K.K.). A seeding density of corn is 66667 seeds/ha. Then, the furrow is spray-treated with an aqueous dispersion of chlorpyrifos and imidacloprid at 125 L/ha so that the application amount is 250 g/ha for chlorpyrifos and imidacloprid for 50 g/ha for thiamethoxam, and then the furrow is closed. This is called a treatment section.

For comparison, corns are seeded by the operation same as that in the treatment section except that chlorpyrifos and imidacloprid are not applied. This is called a non-treatment section.

In any section, four places are arranged by a randomized block method, with one place having an area of 45 m² (15 m×3 m).

17 days after application of chlorpyrifos and imidacloprid, the number of corn plants germinated is investigated, with central two rows of four rows of seeded furrows as an investigation section, for the treatment section and the non-treatment section.

165 days after application of chlorpyrifos and imidacloprid, the number of corn plants lodged due to damage by *Diabrotica virgifera* virgifera and *Agriotes lineatus* in the rows of the treatment section and the non-treatment section where the number of corn plants germinated is investigated, a lodge rate is calculated in accordance with the following equation, and then an average lodge rate for the four investigation sections is determined.

Lodge rate(%)=[(number of corn plants lodged)/ (number of corn plants germinated)]×100

As a result, the treatment section shows a low lodge rate as compared to the non-treatment section, and is found to have reduced damage by harmful organisms in corn cultivation.

Example 6

A chemical fertilizer (N:P:K=15:15:15) is applied to the soil surface of a cultivated land at 300 kg/ha, and the cultivated land is then plowed.

7 days after fertilization, for suppressing generation of weeds, the soil surface of the whole cultivated land is spray-treated with a mixed liquid chemical of thiencarbazone-methyl and isoxaflutole, each of which being a herbicide, at 150 L/ha so that the application amounts of thiencarbazone-methyl and isoxaflutole are 9.2 g/ha and 23 g/ha, respectively.

21 days after fertilization, using a pneumatic seeder (disk furrow opener) equipped with a power sprayer, a cultivated land is ditched at intervals of 75 cm to a depth of 3 cm from the soil surface, and a chlorpyrifos granule is applied to the furrow such that the application amount of chlorpyrifos is 500 g/ha. After application, corns (Zea Mays: hybrid variety) with which treated with thiuram, are seeded in the furrow 20 cm apart in rows. A seeding density of corn is 70000 seeds/ha. In parallel with seeding of corn, the furrow is spray-treated with an aqueous dispersion of thiamethoxam and cyprosulfamide which is a safener at 150 L/ha so that the application amount is 100 g/ha for thiamethoxam and 15 g/ha for cyprosulfamide, with the liquid chemical being in direct contact with the seed, and a soil on the side of the furrow is then gathered together to close the furrow. This is called a treatment section.

For comparison, corns are seeded by the operation same as that in the treatment section except that chlorpyrifos and thiamethoxam are not applied. This is called a non-treatment section.

In any section, four places are arranged by a randomized block method, with one place having an area of 45 m² (15 m×3 m).

17 days after application of chlorpyrifos and thiamethoxam, the number of corn plants germinated is investigated, with central two rows of four rows of seeded furrows as an investigation section, for the treatment section and the non-treatment section. 165 days after application of chlorpyrifos and thiamethoxam, the number of corn plants lodged due to damage by *Diabrotica virgifera* virgifera and *Agriotes lineatus* in the rows of the treatment section and the non-treatment section where the number of corn plants germinated is investigated, a lodge rate is calculated in accordance with the following equation, and then an average lodge rate for the four investigation sections is determined.

Lodge rate(%)=[(number of corn plants lodged)/ (number of corn plants germinated)]×100

As a result, the treatment section shows a low lodge rate as compared to the non-treatment section, and is found to have reduced damage by harmful organisms in corn cultivation.

What is claimed is:

1. A method for reducing damage by harmful organisms in corn cultivation, the method comprising the steps of:
    A) making a furrow in a cultivated land; B) seeding corn into the furrow formed in the foregoing step; C) applying to the furrow one or more selected from the below-mentioned compound group (I) and chlorpyrifos; and D) closing the furrow, wherein the steps are performed in a sequential order of A), C), B) and D);
    the compound group (I): the group consisting of clothianidin, thiamethoxam, imidacloprid and thiacloprid.

2. The method according to claim 1, wherein applying one or more selected from the compound group (I) and chlorpyrifos is a step of applying a composition containing the one or more selected from the compound group (I) and a composition containing chlorpyrifos.

3. The method according to claim 2, wherein the composition containing the one or more selected from the compound group (I) is a granule ormicro-granule containing the one or more selected from the compound group (I).

4. The method according to claim 2, wherein the composition containing the one or more selected from the compound group (I) is an aqueous dispersion or aqueous solution containing the one or more selected from the compound group (I).

5. The method according to claim 2, wherein the composition containing chlorpyrifos is a granule or micro-granule containing chlorpyrifos.

6. The method according to claim 2, wherein the composition containing chlorpyrifos is an aqueous dispersion or aqueous solution of chlorpyrifos.

7. The method according to claim 4, wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains the one or more selected from the compound group (I).

8. The method according to claim 6, wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate or a dry flowable which contains chlorpyrifos.

9. The method according to claim 1, wherein applying the one or more selected from the compound group (I) and chlorpyrifos is a step of applying a composition containing the one or more selected from the compound group (I) and chlorpyrifos.

10. The method according to claim 9, wherein the composition containing the one or more selected from the compound group (I) and chlorpyrifos is a granule or micro-granule containing the one or more selected from the compound group (I) and chlorpyrifos.

11. The method according to claim 9, wherein the composition containing the one or more selected from the compound group (I) and chlorpyrifos is an aqueous dispersion or aqueous solution containing the one or more selected from the compound group (I) and chlorpyrifos.

12. The method according to claim 11, wherein the aqueous dispersion or aqueous solution is an aqueous dispersion or aqueous solution obtained by dispersing or dissolving in water a water soluble powder, a wettable powder, a water dispersible granule, a soluble concentrate, a microcapsule, an emulsifiable concentrate, a concentrated emulsion, a microemulsion, a suspoemulsion, an oil miscible liquid, a suspension concentrate ora dry flowable which contains the one or more selected from the compound group (I) and chlorpyrifos.

13. The method according to claim 1, wherein the land is ditched to a depth of 1 to 10 cm.

14. The method according to claim 1, wherein ditching is performed using a disk furrow opener.

15. The method according to claim 1, wherein the seeding is performed using a pneumatic seeder.

16. The method according to claim 3, wherein the composition containing chlorpyrifos is a granule or microgranule containing the chlorpyrifos.

17. The method according to claim 4, wherein the composition containing chlorpyrifos is a granule or microgranule containing the chlorpyrifos.

18. The method according to claim 3, wherein the composition containing chlorpyrifos is an aqueous dispersion or aqueous solution of the chlorpyrifos.

19. The method according to claim 4, wherein the composition containing chlorpyrifos is an aqueous dispersion or aqueous solution of the chlorpyrifos.

20. The method according to claim 2, wherein the land is ditched to a depth of 1 to 10 cm.

\* \* \* \* \*